US006409763B1

(12) United States Patent
Brady

(10) Patent No.: US 6,409,763 B1
(45) Date of Patent: Jun. 25, 2002

(54) IRIS-SUPPORTED INTRAOCULAR LENSES OPTICS AND RIGID FIXATION MEMBERS

(75) Inventor: Daniel G. Brady, San Juan Capistrano, CA (US)

(73) Assignee: Allergan Sales, Inc, Irvine, CA (US)

( * ) Notice: Subject to any disclaimer, the term of this patent is extended or adjusted under 35 U.S.C. 154(b) by 0 days.

(21) Appl. No.: 09/943,558

(22) Filed: Aug. 30, 2001

(51) Int. Cl.[7] .................................................. A61F 2/16
(52) U.S. Cl. ....................................... 623/6.43; 623/6.4
(58) Field of Search ............................... 623/6.11, 6.38, 623/6.4, 6.43, 6.47

(56) References Cited

U.S. PATENT DOCUMENTS 5,192,319 A * 3/1993 Worst ........................ 623/6.43
6,152,959 A * 11/2000 Portney ..................... 623/6.51
6,193,750 B1 * 2/2001 Cumming .................. 623/6.43
2001/0005794 A1 * 6/2001 Cumming .................. 623/6.43

* cited by examiner

*Primary Examiner*—Dinh X. Nguyen
(74) *Attorney, Agent, or Firm*—Stout, Uxa, Buyan & Mullins, LLP; Frank J. Uxa

(57) ABSTRACT

An iris-supported intraocular lens having an optic portion and a plurality of fixation members coupled thereto. Each fixation member has a pair of pincer arms that separate outward of the optic and converge toward one another at aligned end tips. One or both of the end tips are covered with a soft sleeve or cap. The IOL is fixed in the anterior chamber of the eye by pinching the iris tissue between the end tips of each pair of pincer arms. The soft sleeves eliminate damage to the iris tissue.

23 Claims, 2 Drawing Sheets

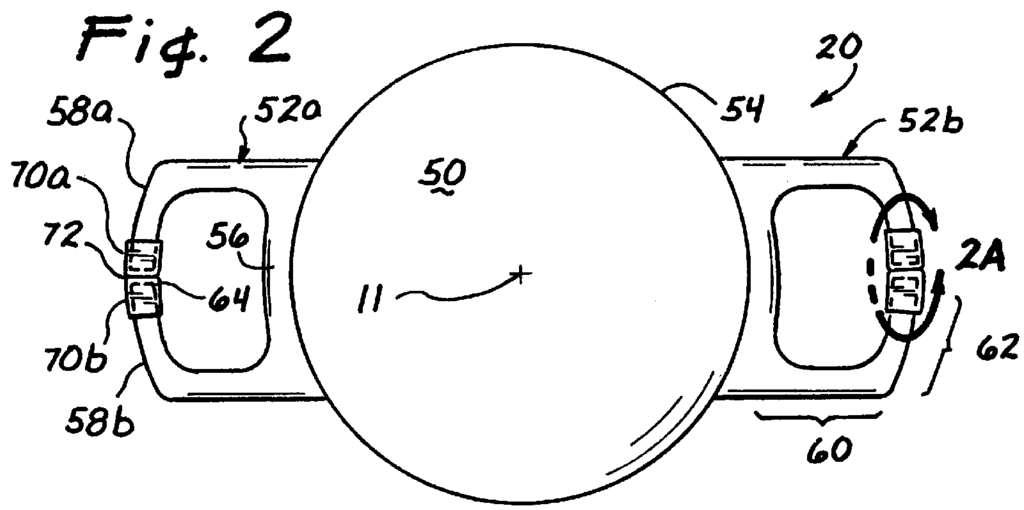
Fig. 2
20
54
58a
52a
52b
50
70a
72
56
2A
64
11
70b
62
58b
60
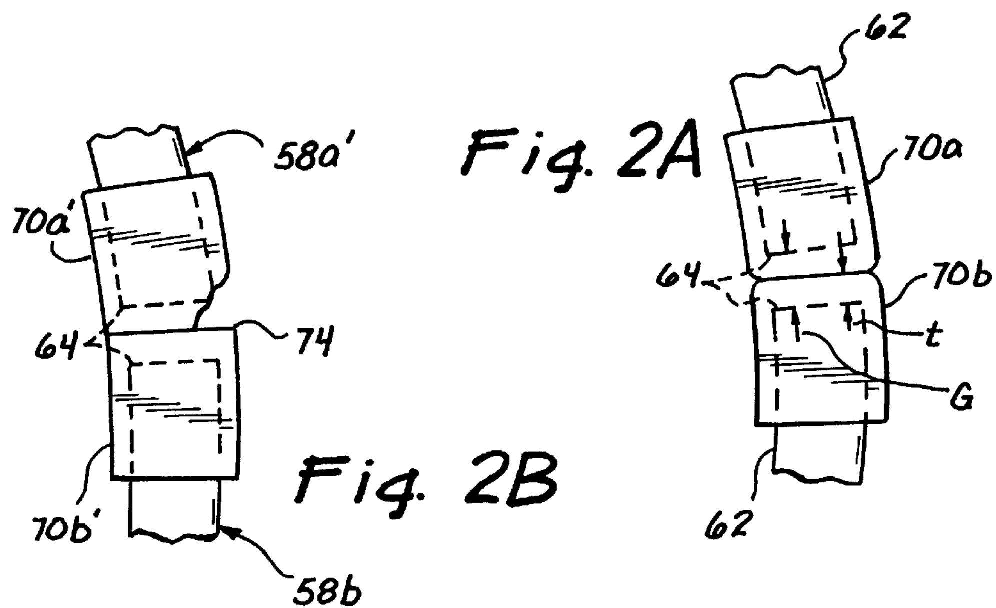
62
58a'
Fig. 2A
70a
70a'
64
70b
64
74
t
G
Fig. 2B
70b'
62
58b
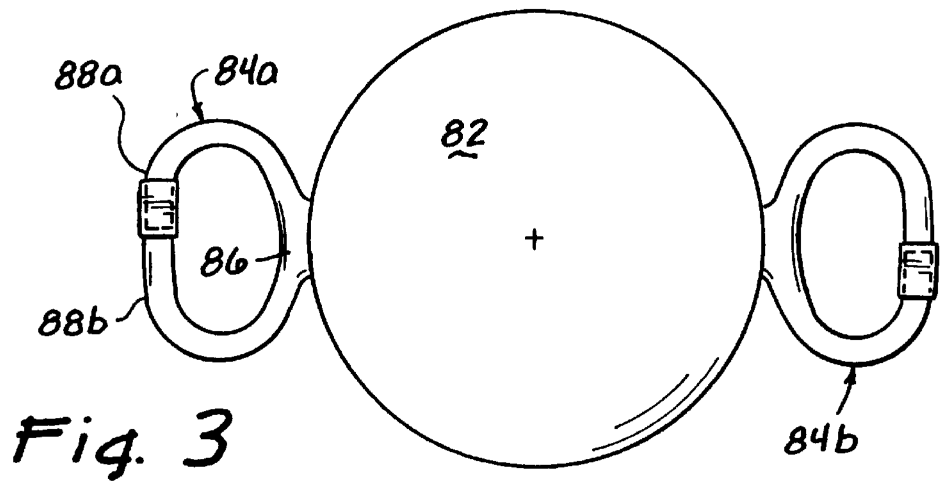
88a
84a
82
86
88b
Fig. 3
84b

IRIS-SUPPORTED INTRAOCULAR LENSES OPTICS AND RIGID FIXATION MEMBERS

BACKGROUND OF THE INVENTION

The present invention relates generally to the field of ophthalmics, more particularly to ophthalmic devices, and still more particularly to ophthalmic devices known as intraocular lenses (IOLs).

Intraocular lenses (IOLs) are commonly used to modify or enhance vision. IOLs can be placed at various positions or locations within the eye. For example, IOLs can be placed in the anterior chamber (AC) of the eye, that is, the region of the eye posterior of the cornea and anterior of the iris. The most common form of such an IOL includes a central lens and outer fixation members or haptics that resiliently contact the annular angle between the cornea and iris.

Although there are substantial advantages to placing the IOL in the anterior chamber of the eye, various complications with angle-supported lenses have been reported. Among other problems, angle-supported anterior chamber IOLs have been reported to cause irritation of the tissue in the angle, and decentration or offsetting displacement away from a preferred optical axis.

Consequently, there has been renewed interest in IOLs constructed for fixation to the iris (some of the earliest IOLs were iris fixated, anterior chamber IOLs), so-called "iris-supported" lenses. By fixing the optic supporting structure to the iris itself, contact with the sensitive filtration angle of the eye is avoided.

Iris fixated IOLs are disclosed in Worst, U.S. Pat. Nos. 4,215,440 and 5,192,319, and in Portney, U.S. Pat. No. 6,152,959. These patents disclose IOLs employing one or more optic fixation members formed having a pair of pincer arms which, acting together, pinch an anterior surface region of the iris. This pinching action detachably attaches the IOL to the iris so that the IOL optic is ideally fixated in the region of the iris opening (i.e., the pupil of the eye). In early designs, the tips of the pincer arms contacted each other, which potentially damaged or even necrosed the iris tissue. In later designs, such as in, Worst, U.S. Pat. No. 5,192,319, the tips of the pincer arms define a gap therebetween which reduces somewhat the tissue damage. However, there is a potential risk that tissue can be damaged by the sharp pincher arms which can puncture the iris tissue.

It would be advantageous to provide iris-supported anterior chamber IOLs which improve on the designs of the prior art.

SUMMARY OF THE INVENTION

New IOLs for implantation in eyes, in particular in anterior chambers of the eyes, have been discovered. The present IOLs are sized and structured to reduce the incidence of one or more known complications in the eye caused by prior iris-supported anterior chamber IOLs.

In one embodiment, the present invention provides an iris-supported intraocular lens for implantation in the anterior chamber of an eye, comprising an optic centered on an optical axis and at least two fixation members extending outward from the optic. Each fixation member defines a pair of separated pincer arms that converge toward one another and terminate at aligned end tips to form a gap therebetween. At least one compliant sleeve covers one of the pincer arm tips and fills the gap. There are desirably two sleeves provided for each fixation member, one sleeve covering each pincer arm end tip. Alternatively, there is only one sleeve provided covering one of the pincer arm end tips.

In a preferred embodiment, each fixation member defines a D-shape with a base region forming the upright of the D and the pincer arms forming the curved portion. Alternatively, each fixation member defines an O-shape with a base region adjacent the optic that is narrower than a separation distance between the pair of pincer arms.

The gap desirably has a dimension G of between about 0.004–0.020 inches (0.102–0.508 mm). The pincer arms are typically made of PMMA, and the sleeve is made of a material that has a durometer of less than about 80, desirably less than about 50 at normal eye temperatures (about 35° C., just under normal body temperature). For example, the sleeve is made of a material selected from the group consisting of silicone, hydrophobic acrylic, and hydrophylic acrylic. The sleeve desirably has abrupt corners at its distal tip to facilitate grasping of tissue.

In another embodiment, an iris-supported intraocular lens for implantation in the anterior chamber of an eye comprises an optic centered on an optical axis, and at least two fixation members extending outward from the optic. In the alternative embodiment each fixation member defines a pair of separated pincer arms of a first material having a first hardness that converge toward one another and terminate at aligned end tips form a gap therebetween, and an interface of a second material positioned within the gap that is more compliant than the first material of the pincer arms. In a preferred embodiment, the interface comprises a sleeve covering one of the pincer arm end tips and filling the gap, and there are desirably two sleeves provided for each fixation member, one sleeve covering each pincer arm end tip. The at least one of the sleeves desirably has an abrupt edge at its distal tip to facilitate grasping of tissue between the sleeves.

Each and every feature described herein, and each and every combination of two or more of such features, is included within the scope of the present invention provided that the features included in such a combination are not mutually inconsistent.

These and other aspects and advantages of the present invention will become apparent in the following detailed description and claims, particularly when considered in conjunction with the accompanying drawings in which like parts bear like reference numerals.

BRIEF DESCRIPTION OF THE DRAWINGS

FIG. 2 is a plan view of the iris-supported intraocular lens of FIG. 1;

FIG. 2A is a detailed view taken within the circle 2A in FIG. 2;

FIG. 2B is a detailed view as in FIG. 2A of an alternative sleeve structure; and FIG. 3 is a plan view of an alternative iris-supported intraocular lens of the present invention.

DESCRIPTION OF THE PREFERRED EMBODIMENTS

Figure 1:
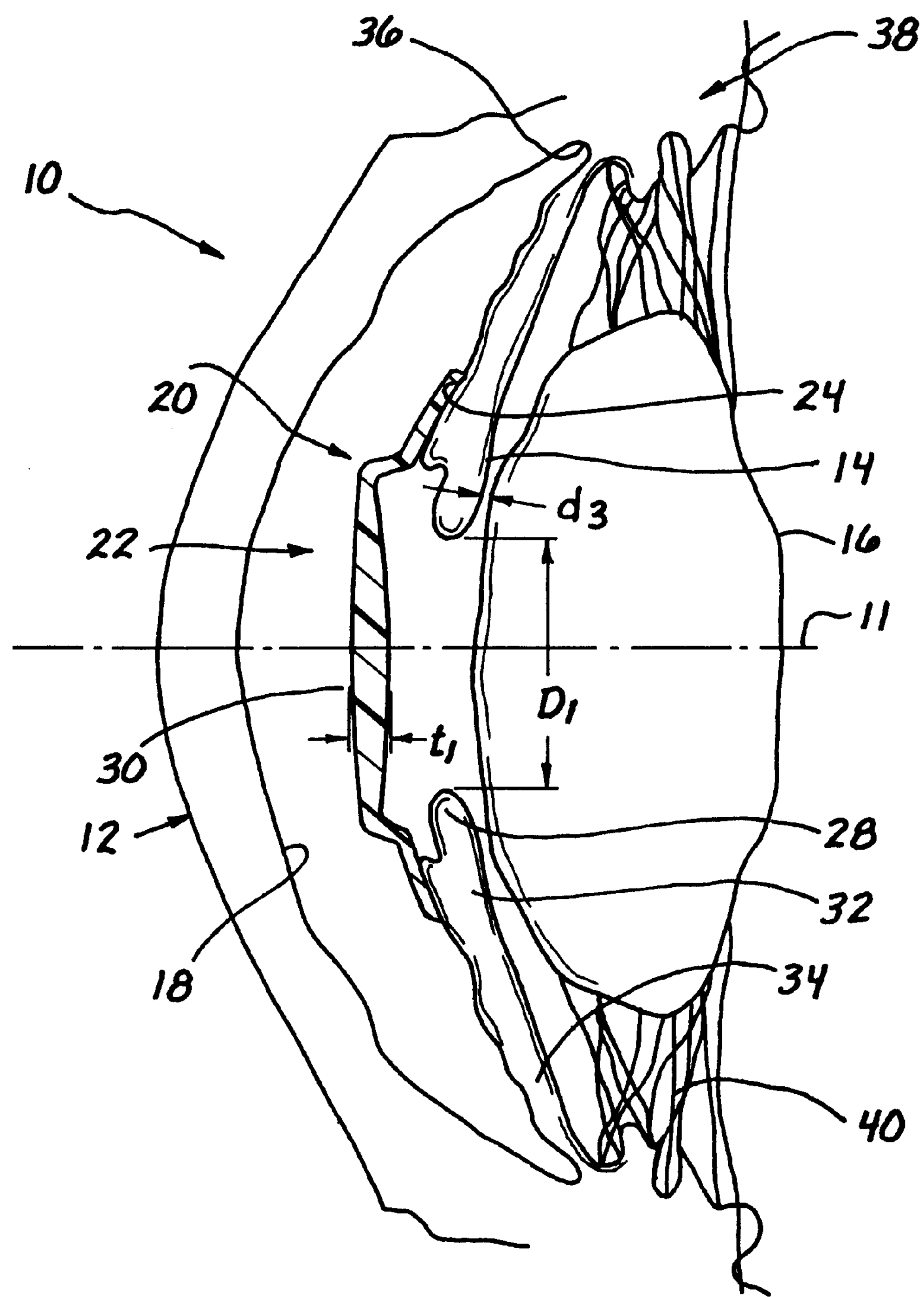
FIG. 1 is a vertical sectional view of a first embodiment of an iris-supported intraocular lens of the present invention.

There is shown in FIG. 1, in vertical cross section, a forward region 10 of a representative human eye having an optical axis 11 (Axis of symmetry), a cornea 12, an iris 14 and an intact, natural crystalline lens 16. A (posterior) corneal endothelium surface 18 is identified on cornea 12.

An iris-supported or iris-fixated intraocular lens (IOL) 20, according to a preferred embodiment of the present invention, is shown implanted in an anterior chamber 22 of eye region 10 (posterior to corneal endothelium surface 18) and fixated, in a manner described below, to an anterior surface 24 of iris 14.

An annular pupiliary spincter region 28 of iris 14 surrounds and controls a pupil or pupiliary opening 30 having a diameter, $D_1$, typically no greater than about 8 mm for normal vision.

Further identified are an annular iris collarette region 32 and an annular pupiliary dilator muscle region 34 of iris 14. An annular chamber angle 36 is identified at a peripheral edge region of iris 14, as is an annular trabecular meshwork 38. An annular ciliary process 40 is indicated at the peripheral attachment of natural lens 16.

As seen in FIG. 1, iris fixated IOL 20 is fixated to iris anterior surface 24 in the general region of iris collarette 32 (the thickest region of iris 14), radially outwardly from pupillary sphincter 28.

With reference to FIGS. 2 and 2A in conjunction with FIG. 1, the IOL 20 includes an optic 50 which has respective anterior and posterior surfaces, and may be constructed as convex-convex (as depicted in FIG. 1), convex-concave, convex-planar, or concave-planar or concave-concave, all such and other configurations being within the scope of the present invention. Optic 50 may advantageously be provided in the diopter range between about −25 and about +30. It is preferred that optic 50 be constructed from an elastically deformable material, such as a silicone or acrylic material, enabling the optic to be folded, rolled or otherwise deformed so that IOL 20 can be implanted through an ocular incision no larger than about 4.0 mm or about 3.5 mm or about 3.0 mm.

The IOL 20 further includes at least two fixation members 52*a,* 52*b* that extend radially outward from the outer edge 54 of the optic 50. Each of the fixation members 52*a,* 52*b* includes a base region 56 attached to the optic 50 and a pair of pincer arms 58*a,* 58*b* extending outward from the base region. As seen to the right side of FIG. 2, each pincer arm 58*a,* 58*b* includes a proximal segment 60 that projects generally radially outward from the base region 56, and a distal segment 62 that extends from the outer end of the proximal segment in a generally circumferential direction with respect to the optical axis 11. Each of the segments 60, 62 has a length that is substantially larger than its width or depth (into the page).

The fixation members 52*a,* 52*b* may be made of various materials typically used for such structures. For instance, a polymethylmethacrylate (PMMA), acrylic, or other such material is suitable. The fixation members 52*a,* 52*b* must have a minimum of stiffness to locate the optic 50 along the natural optical axis.

The distal segments 62 of the two pincer arms 58*a,* 58*b* converge toward one another and terminate at aligned end tips 64, as seen best in the enlarged view of FIG. 2A. The pair of pincer arms 58*a,* 58*b* on each fixation member 52*a,* 52*b* thus forms a "C" shape, with the distal segments 62 defining the upright of the "C." The base region 56 is about as wide as the widest separation distance between the pincer arms 58*a,* 58*b* such that the entire fixation member 52 resembles a "D."

The distal segments 62 do not meet in the middle, but instead are spaced apart by a gap G (FIG. 2A). The gap G is desirable between about 0.004–0.020 inches (0.102–0.508 mm).

In contrast to the prior art iris-supported IOLs, the gap G is not empty but is instead filled with the material from one or more compliant caps or sleeves, such as the sleeves 70*a,* 70*b* seen in FIG. 2, over the tips 64 of the pincer arms 58*a,* 58*b*. When there are two such sleeves 70*a,* 70*b* over both tips 64, and they are identical, they meet along a mid-plane 72. In a preferred embodiment, the wall thickness t of each sleeve 70*a,* 70*b* (at least between the tips 64) is about one-half of the gap G. As a consequence, the material of the sleeves 70*a,* 70*b* remains substantially uncompressed when the IOL is not in use. Alternatively, the wall thickness t of each sleeve 70*a,* 70*b* may be such that some compression of the material of the sleeves 70*a,* 70*b* occurs when the IOL is not in use.

FIG. 2B illustrates alternative sleeves 70*a*', 70*b*' over the tips 64 of the pincer arms 58*a,* 58*b*. Instead of being rounded at their ends, the sleeves 70*a*', 70*b*' have right-angled or otherwise abrupt or sharp corners 74 at their ends, thus enhancing their ability to grasp iris tissue therebetween. The sharp corners are desirably continuous around the tip of each sleeve 70*a*', 70*b*', although intermittent points or teeth may be used.

In use, the pincer arms 58*a,* 58*b* are used to clamp and grasp iris tissue on opposed sides of the IOL 20 to fixate the IOL within the anterior chamber, as seen schematically in FIG. 1. The material of the sleeves 70*a,* 70*b* is desirably highly compliant so that tissue damage or necrosis is eliminated. For example, the sleeves 70*a,* 70*b* may be made of a silicone, a hydrophobic acrylic, a hydrophylic acrylic, or other such biocompatible material suitable for long-term implantation in the ocular environment. The softness or compliance of the material is typically measured by a durometer value at normal eye temperatures (about 35° C., just under normal body temperature), and is desirably between about 0 to about 80 and, more preferably between about 5 to about 50. Desirably, the shape of the facing tips of at least one of the sleeves 70*a,* 70*b* is such that the sleeves cooperate to grasp the iris tissue therebetween.

It will be understood by those of skill in the art that the material properties of the sleeves 70*a,* 70*b* and the gap G between the tips 64 factor into the amount of compression applied to the iris tissue, although the implant technique also plays a role. The IOL 20 is thus designed so that the surgeon can reliably implant it using the pincer arms 58*a,* 58*b* without undue compression and attendant tissue damage.

It should also be mentioned that the soft covering of the sleeves 70*a,* 70*b* over the tips 64 further reduces the instance of tissue damage because it covers over any sharp corners of the harder tips. Because of the ability of the soft material to deflect, the surgical technique to entrap tissue between the pincer arms is simplified and made more reliable. Furthermore, alternatives to the sleeve structure are contemplated, as long as the end tips of the pincer arms compress a material therebetween (other than the iris tissue) that is more compliant than the material of the end tips. For example, end plugs that are adhered or otherwise fastened to the tips of the pincer arms are contemplated.

FIG. 3 illustrates an alternative embodiment of an iris-supported IOL 80 having an optic 82 and a pair of oppositely-directed fixation members 84. Each fixation member 84 differs from the fixation members 52 in FIG. 2 in that a base region 86 is narrower than the separation distance between a pair of pincer arms 88*a,* 88*b* extending outwardly therefrom. Each fixation member 84 thus forms an "O" shape. This shape facilitates folding of the IOL 80 (about a horizontal line through the center thereof).

As before, the tips of the pincer arms 88*a,* 88*b* are separated by a gap, with a compliant material filling the gap.

Instead of a sleeve covering the tips of both pincer arms 88*a,* 88*b,* only one such sleeve 90 is provided. In this manner, the pincer arms 88*a,* 88*b* compress tissue therebetween with the benefit of the compliance of the material of the sleeve 90, though one of the pincer arms comes into direct contact with the tissue.

While this invention has been described with respect to various specific examples and embodiments, it is to be understood that the invention is not limited thereto and that it can be variously practiced within the scope of the following claims.

What is claimed is:

1. An iris-supported intraocular lens for implantation in the anterior chamber of an eye, the intraocular lens comprising:

an optic centered on an optical axis;

at least two fixation members extending outward from the optic, each fixation member defining a pair of separated pincer arms that converge toward one another and terminate at aligned end tips to form a gap therebetween; and at least one compliant sleeve covering one of the pincer arm tips and filling the gap.

2. The intraocular lens of claim 1, wherein there are two sleeves provided for each fixation member, one sleeve covering each pincer arm end tip.

3. The intraocular lens of claim 1, wherein there is only one sleeve provided covering one of the pincer arm end tips.

4. The intraocular lens of claim 1, wherein each fixation member defines a D-shape with a base region forming the upright of the D and the pincer arms forming the curved portion.

5. The intraocular lens of claim 1, wherein each fixation member defines an O-shape with a base region adjacent the optic that is narrower than a separation distance between the pair of pincer arms.

6. The intraocular lens of claim 1, wherein the gap has a dimension G of between about 0.004–0.020 inches (0.102–0.508 mm).

7. The intraocular lens of claim 1, wherein the pincer arms are made of PMMA.

8. The intraocular lens of claim 1, wherein the sleeve is made of a material that has a durometer of less than about 80.

9. The intraocular lens of claim 8, wherein the sleeve is made of a material that has a durometer of less than about 50.

10. The intraocular lens of claim 1, wherein the sleeve is made of a material selected from the group consisting of:

silicone;

hydrophobic acrylic; and hydrophylic acrylic.

11. The intraocular lens of claim 1, wherein the sleeve has abrupt corners at its distal tip.

12. An iris-supported intraocular lens for implantation in the anterior chamber of an eye, the intraocular lens comprising:

an optic centered on an optical axis;

at least two fixation members extending outward from the optic, each fixation member defining a pair of separated pincer arms of a first material having a first hardness that converge toward one another and terminate at aligned end tips to form a gap therebetween; and an interface of a second material positioned within the gap that is more compliant than the first material of the pincer arms.

13. The intraocular lens of claim 12, wherein the interface comprises a sleeve covering one of the pincer arm end tips and filling the gap.

14. The intraocular lens of claim 12, wherein there are two sleeves provided for each fixation member, one sleeve covering each pincer arm end tip.

15. The intraocular lens of claim 14, wherein at least one of the sleeves has an abrupt edge at its distal tip to facilitate grasping of tissue between the sleeves.

16. The intraocular lens of claim 14, wherein the sleeves include abrupt corners which are continuous around the distal tips of the sleeves.

17. The intraocular lens of claim 12, wherein the gap has a dimension G of between about 0.004–0.020 inches (0.102–0.508 mm).

18. The intraocular lens of claim 12, wherein the first material is PMMA.

19. The intraocular lens of claim 12, wherein the second material has a durometer of less than about 80 at normal eye temperatures.

20. The intraocular lens of claim 19, wherein the second material has a durometer of less than about 50 at normal eye temperatures.

21. The intraocular lens of claim 12, wherein the second material is selected from the group consisting of:

silicone;

hydrophobic acrylic; and hydrophylic acrylic.

22. The intraocular lens of claim 19, wherein the first material is PMMA.

23. The intraocular lens of claim 22, wherein the second material is selected from the group consisting of:

silicone;

hydrophobic acrylic; and hydrophylic acrylic.

* * * * *